(12) United States Patent
Rivera

(10) Patent No.: US 11,642,275 B2
(45) Date of Patent: May 9, 2023

(54) PORTABLE SEX ARTICLE

(71) Applicant: Rico Enterprises, LLC, Clayton, NC (US)

(72) Inventor: Patrick B. Rivera, Clayton, NC (US)

(73) Assignee: Rico Enterprises, LLC, Clayton, NC (US)

( * ) Notice: Subject to any disclaimer, the term of this patent is extended or adjusted under 35 U.S.C. 154(b) by 471 days.

(21) Appl. No.: 16/790,156

(22) Filed: Feb. 13, 2020

(65) Prior Publication Data
US 2021/0251843 A1 Aug. 19, 2021

(51) Int. Cl.
| | |
|---|---|
| *A61H 19/00* | (2006.01) |
| *A47G 9/10* | (2006.01) |
| *A47G 9/02* | (2006.01) |
| *A61F 5/41* | (2006.01) |
| *A61F 5/451* | (2006.01) |
| *A47G 9/00* | (2006.01) |
| *A47G 9/04* | (2006.01) |

(52) U.S. Cl.
CPC ............ *A61H 19/32* (2013.01); *A47G 9/0253* (2013.01); *A47G 9/1045* (2013.01); *A61F 5/41* (2013.01); *A61F 5/451* (2013.01); *A61H 19/00* (2013.01); *A61H 19/30* (2013.01); *A61H 19/50* (2013.01); *A47G 9/04* (2013.01); *A47G 2009/002* (2013.01); *A47G 2009/1018* (2013.01); *A61F 2005/411* (2013.01); *A61H 2201/0134* (2013.01)

(58) Field of Classification Search
CPC ........ A61H 19/00; A61H 19/30; A61H 19/32; A61H 19/44; A61H 19/50; A61H 2201/0134; A61H 2201/0157; A61H 2201/169; A61H 2205/087
See application file for complete search history.

(56) References Cited

U.S. PATENT DOCUMENTS

| | | | |
|---|---|---|---|
| 10,251,808 B1* | 4/2019 | Theis | A47C 15/008 |
| 2004/0122287 A1 | 6/2004 | Minigh | |
| 2007/0214572 A1* | 9/2007 | Buben | A61H 19/00 5/632 |
| 2018/0104088 A1* | 4/2018 | Ishikawa | A61H 21/00 |

FOREIGN PATENT DOCUMENTS

| | | |
|---|---|---|
| DE | 102006047688 A1 | 4/2008 |
| EP | 2382955 A1 | 11/2011 |

OTHER PUBLICATIONS

"onahole.eu" webpage, Review of "Insert Air Pillow" by Tamatoys, Jul. 19, 2016. (Year: 2016).*

* cited by examiner

*Primary Examiner* — Christine H Matthews
(74) *Attorney, Agent, or Firm* — Vedder Price P.C.

(57) ABSTRACT

Disclosed embodiments provide a portable sex article. The article includes a soft hollow case (which, in some embodiments, is a pillow case). The case is specially designed with a holster formed on a first side the case. The holster is adapted to secure a sex simulation device such as an artificial vagina or dildo. The holster extends into an interior region of the case, and may have a securing mechanism such as elastic bands or a hook-and-loop fastener to secure a sex simulation device in place. A human image is imparted on the case, such as by a textile printing process. The human image can be a photograph or illustration. The human image includes a rendering of an anatomical orifice, such as an anus, vagina, and/or mouth. The human image is oriented such that the anatomical orifice is aligned with the holster.

19 Claims, 12 Drawing Sheets

PORTABLE SEX ARTICLE

FIELD

The present invention relates to a sexual interaction device.

BACKGROUND

For promoting sexual health in people with penises, recent studies have suggested promoting frequent ejaculation, since these studies have found a correlation of a high frequency of ejaculation with a reduced risk of prostate cancer. Other benefits, such as improved performance and erection duration are also attributed to masturbation in some studies. Orgasms have also been attributed to benefits, such as stress-relief, improved relaxation, and menstrual cramp relief in people with vaginas. Sexual stimulation devices such as "sex dolls" exist for providing an enhanced experience during masturbation or during play with one or more partners. However, these items have various shortcomings. It is therefore desirable to have improvements in sex articles.

SUMMARY

In one embodiment, there is provided a sex article, comprising: a soft hollow case; a holster formed on a first side of the soft hollow case, wherein the holster extends into an interior region of the soft hollow case; an image imparted on the soft hollow case, wherein the image includes a rendering of an anatomical orifice, wherein the image is oriented such that the anatomical orifice is aligned with the holster.

In another embodiment, there is provided a sex article, comprising: a soft hollow case; a holster formed on a first side of the soft hollow case, wherein the holster extends into an interior region of the soft hollow case; an image imparted on the soft hollow case, wherein the image is oriented such that a location of an anatomical orifice of the image is aligned with the holster.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

The drawings are not necessarily to scale. The drawings are merely representations, not necessarily intended to portray specific parameters of the invention. The drawings are intended to depict only example embodiments of the invention, and therefore should not be considered as limiting in scope. In the drawings, like numbering may represent like elements. Furthermore, certain elements in some of the figures may be omitted, or illustrated not-to-scale, for illustrative clarity.

DETAILED DESCRIPTION

Figure 1A:
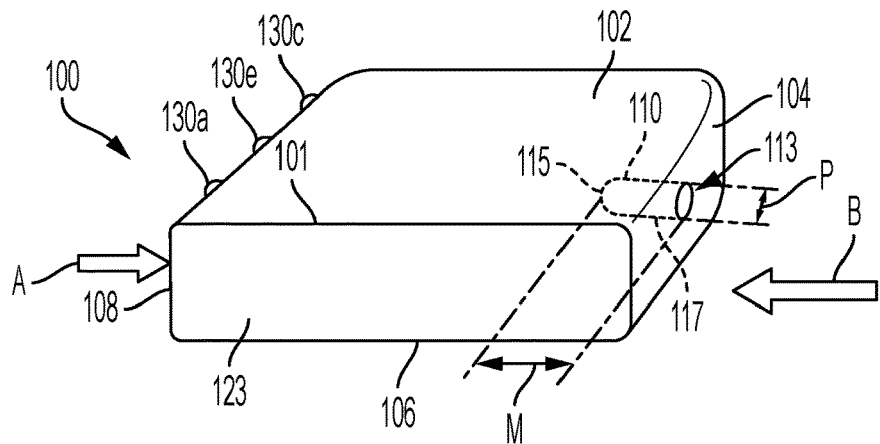
FIG. 1A shows a side perspective view of an article in accordance with embodiments of the present invention showing the holster.

Sex simulation devices that serve as an artificial vagina (such as the product sold under the registered trademark, Fleshlight®, owned by Steve Shubin, an individual) or dildo for the purposes of masturbation, or sexual play with one or more partners, are becoming very popular due to their affordability, easy storage, and in some cases, highly realistic feel. These devices help a person achieve sexual pleasure. Masturbation and sex have many important benefits including muscle training, stress relief, menstrual cramp relief, and studies have shown that higher numbers of ejaculations lead to a lower risk of prostate cancer.

Disclosed embodiments provide a portable sex article. The article includes a soft hollow case, or a soft substantially hollow case. In some embodiments, the case is a pillowcase. A holster formed on a first side of the case. The holster is adapted to secure a sex simulation device such as an artificial vagina or a dildo. Embodiments provide a case that is light and portable while the case is not filled, so the case can be rolled up or folded for storage or travel. Conventional sex dolls are heavy and difficult to move.

The case or holster may be made from any suitable soft material. "Soft" herein means foldable, collapsible, or rollable, such as fabric, textile, leather, rubber, vinyl, cotton, polyester, nylon, vinyl, soft plastic, silk, satin, rubber, a combination thereof, or other suitable material. In some embodiments, the material can be porous. In some embodiments, the material can be non-porous. In some embodiments, the material is washable. In some embodiments, the material is waterproof. In some embodiments, the material is water-resistant.

Conventional sex simulation devices adapted for penis use are usually substantially cylindrical in shape, have a hard exterior wall, such as a hard plastic, and a soft interior wall made from silicone, TPE, or other suitable material. An interior canal is formed by the soft interior wall. During use, a user inserts their penis into the canal via an opening. Conventional sex stimulation devices adapted for vaginal or anal use are usually substantially cylindrical in shape, having a portion for penetrating the vagina or anus. They made be made from, or include, plastic, silicone, TPE, metal, or other suitable material.

The holster of embodiments extends into an interior region of the case, and may have a fastener attached thereto such as elastic bands, a strap, a hook-and-loop fastener (such as the product sold under the registered trademark Velcro®, owned by Velcro Industries B.V., LLC), or other suitable fastener, to secure the sex simulation device in place. The holster holds the sex simulation device temporarily, until the user chooses to remove the device therefrom. The holster is preferably made from a soft material, such that it may be collapsed when the article is not in use for folding, rolling, or other collapsing to enable easy storage or transport. In some embodiments, the holster is made from a soft material such as fabric, textile, leather, rubber, vinyl, cotton, polyester, nylon, vinyl, soft plastic, silk, satin, rubber, a combination thereof, or other suitable material. In some embodiments, it can be the same material as the case, or can be made from a different material. The holster may be sewn on to the case or, or otherwise attached thereto.

An image, such as a human image, is imparted on the case, such as by a textile printing process. The human image can be a photograph, graphic, illustration, or other suitable depiction. The human image includes a rendering of an anatomical orifice, such as an anus, vagina, and/or mouth. The human image is oriented such that the anatomical orifice is aligned with the holster. As an example, the human image may be oriented such that the holster location is substantially located where the vagina, anus, or mouth of the human image is located. This can provide an enhanced visual experience during use, as it mimics imagery that may be observed during sexual intercourse with a partner. In some embodiments, rather than a human image, another suitable image may be included.

To use embodiments of the present invention, the user inserts and secures, via the fastener, a sex simulation device into the holster. The user then inserts fill material, such as pillows into the interior of the case, and seals the opening of the pillowcase using a closure. The user then inserts their penis into the canal of the sex stimulation device (or slides an insertable portion of the sex simulation device into their vagina or anus) held by the holster of the case. The imagery on the case resembles imagery that may be observed during sexual intercourse with a partner.

In some embodiments, standard, pre-set images may be used. In other embodiments, the images may be customizable. In such embodiments, a user may provide an image of their own choosing that may then be scaled and registered to fit on the case such that the holster is aligned with an anatomical orifice on the human image that is imparted onto the case. In yet other embodiments with customization, a user may specify attributes, such as hair color, hair length, skin tone, etc. to describe characteristics of a human image that they wish to be imparted onto the article.

Thus, with disclosed embodiments, there is provided a sex article that is light, portable, discrete, and can enhance a user's overall experience and create a much more realistic "partner" that can easily travel with in privacy and can be easily and quickly stored away when not in use.

Reference throughout this specification to "one embodiment," "an embodiment," "some embodiments", "embodiments," or similar language means that a particular feature, structure, or characteristic described in connection with the embodiment is included in at least one embodiment of the present invention. Thus, appearances of the phrases "in one embodiment," "in an embodiment," "in some embodiments", "in embodiments," and similar language throughout this specification may, but do not necessarily, all refer to the same embodiment.

Moreover, the described features, structures, or characteristics of the invention may be combined ("mixed and matched") in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents. Reference will now be made in detail to the preferred embodiments of the invention.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, and/or elements.

For the purposes of disclosure, the word, "substantially" is defined as "for the most part". It means "to a great extent," but having some room for some minor variation.

FIG. 1A shows a side perspective view of an article 100 in accordance with embodiments of the present invention. A case 101 has a front side 104, a top side 102, a bottom side 106, and a back side 108. Front side 104 and back side 108 are oriented opposite, or substantially opposite, one-another. The back side 108 of the case 101 is open, having a fill insertion opening indicated by arrow A, such that fill material can be inserted into the case 101. In some embodiments, the back side 108 may be temporarily closed using a closure (portions of which are shown at 130a, 130c, and 130f). The closure may include, but is not limited to, a zipper, buttons, hook-and-loop-fastener, drawstring, buttons, snaps, a combination thereof, or other suitable closure. The closure is re-openable and re-sealable for multiple usage instances. Note that, in some alternative embodiments, the fill insertion opening, may be on a side of the case 101, rather than the back side 108.

In some embodiments, the fill material can include one or more standard-sized (bed) pillows (20 inches by 26 inches), queen-sized (bed) pillows (20 inches by 30 inches), king-sized (bed) pillows (20 inches by 36 inches), other sized pillows, foam pieces, loose fill (e.g. pellets), sand, foam balls, or other suitable fill material. The article is configured such that feasible fill material shall not be solely or primarily gaseous, in contrast to a "blow-up doll." Pillows typically include a soft exterior sheath and a cotton, feather, foam, polyester, gel, or other material on the inside.

A holster 110 is formed in the front side 104 of the case 101. The holster 110 may have a closed surface at its backside 115 and an opening 113 at the front. Holster has a side 117, which may be substantially continuous and substantially cylindrical in shape between the backside 115 and opening 113. Holster may be attached to interior side 123 (FIG. 1B) (or in some embodiments, exterior and pushed into the interior) of the front side 104 of case 101 at a seam 125 (FIG. 1B) (via threads, adhesive, buttons, or other attachment). The portions of the holster are shown in broken lines in FIG. 1A to represent that they are covered in the view by another item (i.e. the walls) of case 101. In some embodiments, the holster 110 is between 2 and 5 inches in width or diameter P and between 6 and 12 inches in length M (between the front side 104 of the case 101 and the backside 115 of the holster). For example, in some embodiments, the dimensions may be 4.5 inches wide by 8.5 inches in length. Note that such dimensions and ranges are examples, and other feasible dimensions are included within the scope of embodiments of the invention.

It should be recognized that the words, "front", "back," and "side" are used for the purposes of description, and not meant to be limiting. In some embodiments, instead of the back being open, one of the sides between the front and back may be open.

Figure 1B:
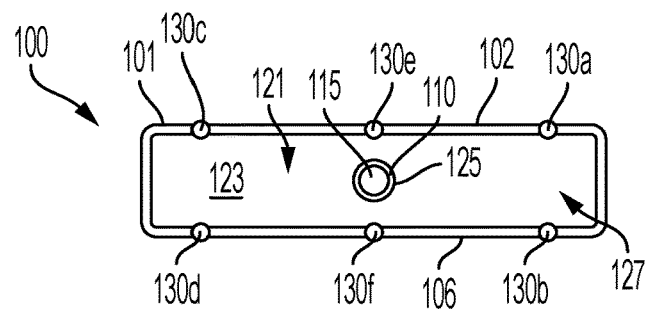
FIG. 1B shows a back plan view of an article with the interior in view.

FIG. 1B shows a back view of article 100 with the fill insertion opening 127 open. The interior space 121 is in view. Closures 130a, 130b and 130c, 130d and 130e and 130f, which in the example, are snaps, are not closed. It should be recognized that in embodiments, more or fewer than three closures may be included. Backside 115 of holster 110 is in view.

Figure 1C:
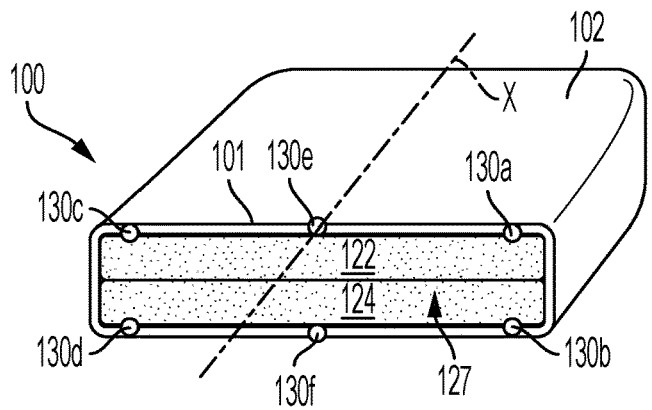
FIG. 1C shows a back perspective view of a filled article in accordance with embodiments of the present invention with fill material present in the interior.

FIG. 1C shows a back perspective view of article 100 with pillows inserted—two pillows 122 and 124, of the four pillows, are in view. In FIG. 1C, the closures 130a, 130b and 130c, 130d and 130e, 130f are not closed. During use, a user pulls 130a to 130b and 130c to 130d and 130e to 130f to close the case. In some embodiments, the case 101 is sized to snuggly accommodate, for example, four standard-sized pillows. In some embodiments, the case 101 is sized to snuggly accommodate, for example, four queen- or king-sized pillows. In some embodiments, more pillows may fit. In some embodiments, the case 101 is sized to snuggly accommodate fewer pillows, or different pillows (such as, for example, a single or two body pillows with dimensions of approximately 20 inches by 54 inches). Accordingly, in some embodiments, the case 101 is substantially the same size (or minimally bigger or smaller) in volume as the combined volume of the total number of pillows meant to be deposited therein. In some embodiments, the case 101 is smaller than such volume when unfilled, but stretchable to the same volume as the combined volume of the total number of pillows meant to be deposited therein.

Figure 1D:
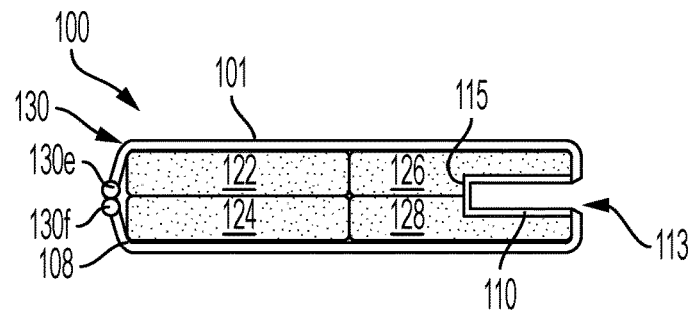
FIG. 1D shows a side cross-section view, cut across line X of FIG. 1C, of a filled article in accordance with embodiments of the present invention.

FIG. 1D shows a side cross-section view, cut along line X of FIG. 1C, of article 100 in accordance with embodiments of the present invention with fill material present. The far wall of the holster 110, as oriented in the figure, is not shown, to emphasize the holster is open (to accept therein a sex simulation device). As shown in FIG. 1B, four pillows, indicated as 122, 124, 126, and 128 are inserted into the case 101, and then a closure 130e attached to 130f is used to seal the case. Thus, embodiments can include fill material disposed within the case.

Figure 1E:
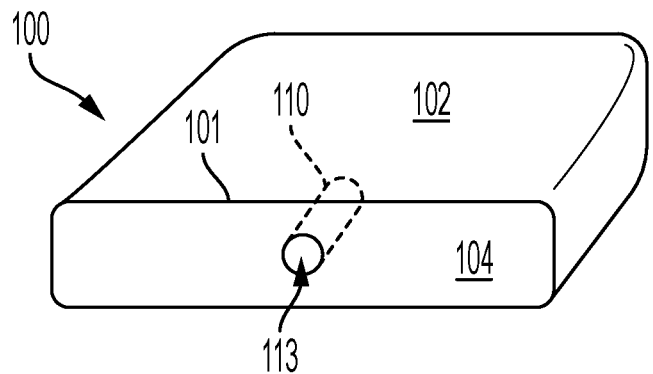
FIG. 1E shows a front perspective view of an article in accordance with embodiments of the present invention showing the holster.

FIG. 1E shows a front perspective view of article 100 in accordance with embodiments of the present invention showing the holster 110, as viewed from the direction of arrow B of FIG. 1A. Formed in front side 104 is a holster 110. In some embodiments, holster 110 has a substantially-cylindrical or conical shape.

Figure 1F:
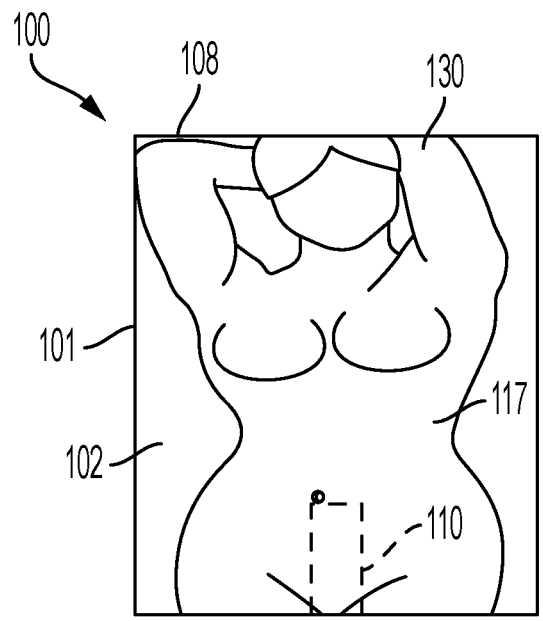
FIG. 1F shows a top-down view of an article in accordance with embodiments of the present invention.

FIG. 1F shows a top-down view of article 100 in accordance with embodiments of the present invention. Case 101 has a first human image 117 imparted on the top side 102 of the case 101. In some embodiments, the human image 117 is a photograph. In some embodiments, the human image 117 is an illustration. In some embodiments, human image 117 is a computer-generated graphic. In embodiments, the human image is formed onto the case by the process of dye-sublimation transfer printing, or other suitable technique. Holster 110 is shown in broken lines to represent that it is beneath the top surface.

Figure 1G:
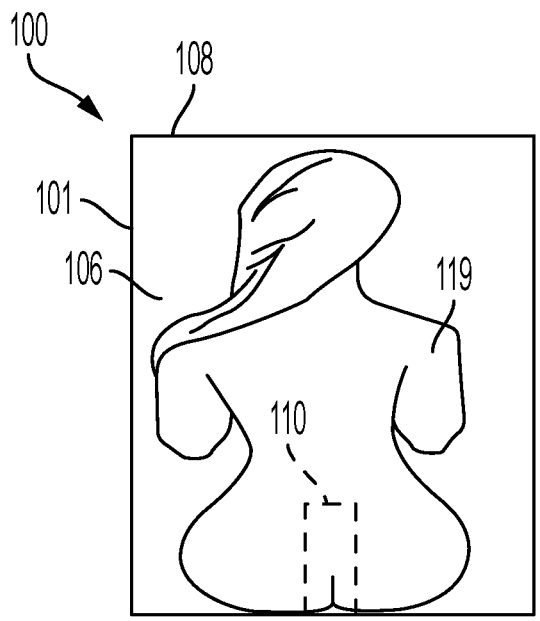
FIG. 1G shows a bottom-up view of an article in accordance with embodiments of the present invention.

FIG. 1G shows a bottom-up view of article 100 in accordance with embodiments of the present invention. In some embodiments, a second human image 119 is imparted on the bottom side 106 of the case 101. In this way, the user can orient the article 100 top-side up to reveal a first image during use, as shown in FIG. 1F, or alternatively, can orient the article 100 bottom-side up to reveal a second image during use. Alternatively, some embodiments may only utilize a human image on one side of the case (e.g., top side 102). In some embodiments, the human image 119 is a photograph. In some embodiments, the human image 119 is an illustration. In some embodiments, human image 119 is a computer-generated graphic. Holster 110 is shown in broken lines to represent that it is beneath the bottom surface.

Figure 2A:
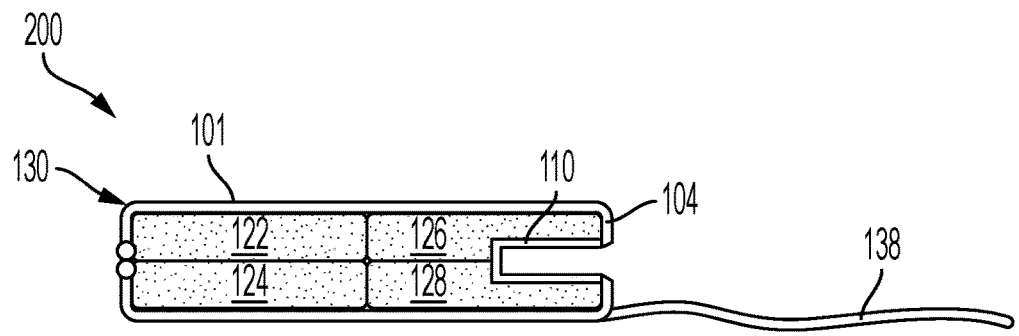
FIG. 2A shows a side cross-section view, cut across line Y of FIG. 2B, of a filled article in accordance with additional embodiments of the present invention.
Figure 2B:
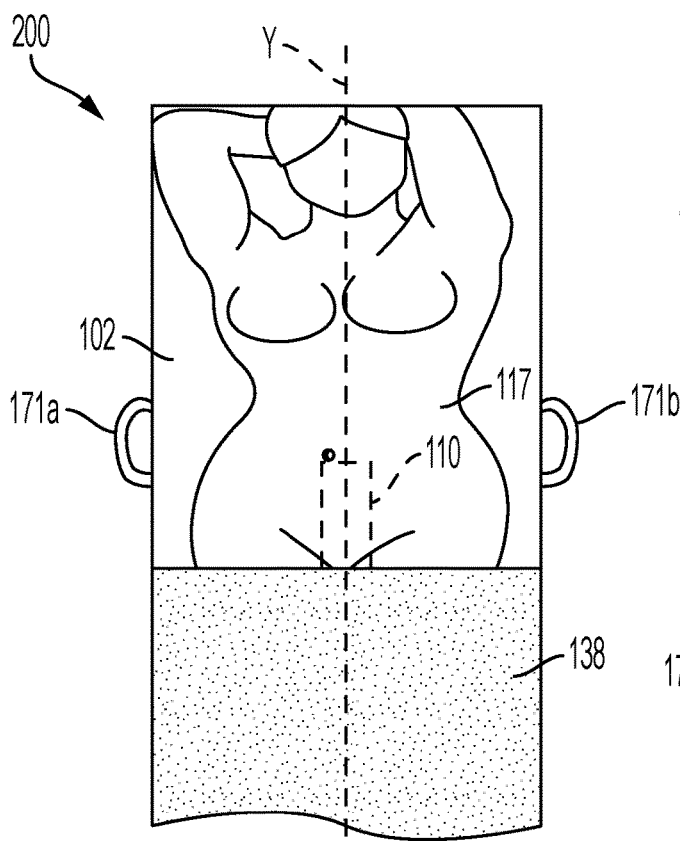
FIG. 2B shows a top-down view of the article of FIG. 2A.

FIG. 2A shows a side cross-section view, cut along line Y of FIG. 2B, of an article 200 having fill material therein in accordance with additional embodiments of the present invention. The far wall of the holster 110, as oriented in the figure, is not shown, to emphasize the holster is open (to accept therein a sex simulation device). Article 200 is similar to article 100, with the addition of a kneepad 138 and handles (FIG. 2B). The kneepad 138 is affixed to, or formed as an extension of, the front side 104 of the case 101. During use, the user may position their knees on the kneepad 138 to provide stability for the article, as well as additional comfort for the user by providing padding for the knees during use. The kneepad may be a soft material, such as (without limitation) fabric, enclosing a soft foam or foam-like material, so as to be comforting to a user's knees. Note that fabric is an example, and any suitable cushioning material is included within the scope of the invention. In some embodiments, the kneepad may be made from the same material as the case 101. The kneepad 138 is rollable or foldable.

FIG. 2B shows a top-down view of the article of FIG. 2A. Optionally, handles, indicated as 171*a* and 171*b* may be formed in the case 101. This allows a user to easily and firmly grasp the article during use. In some embodiments, the handles may be made from the same soft material as the case, or a rope, cord, or other suitable material. The handles may also serve to allow a user to easily carry the unfilled article for easy mobility.

Figure 2C:
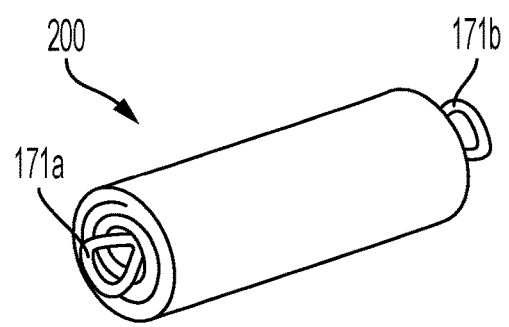
FIG. 2C shows the article of FIG. 2B, without fill material therein, rolled up.

FIG. 2C is a perspective view of a representation of the article of FIG. 2B, without fill material therein, collapsed and rolled up.

Figure 2D:
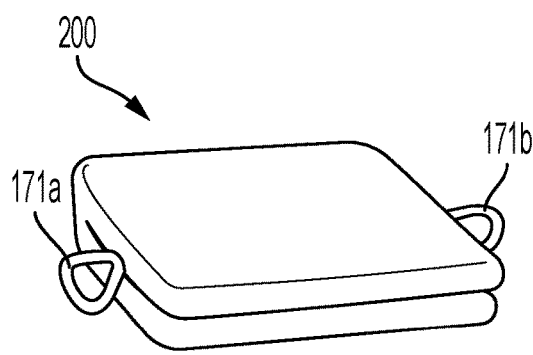
FIG. 2D shows the article of FIG. 2D, without fill material therein, folded up.

FIG. 2D shows a perspective view of a representation of the article of FIG. 2B, without fill material therein, collapsed and folded up.

Figure 3A:
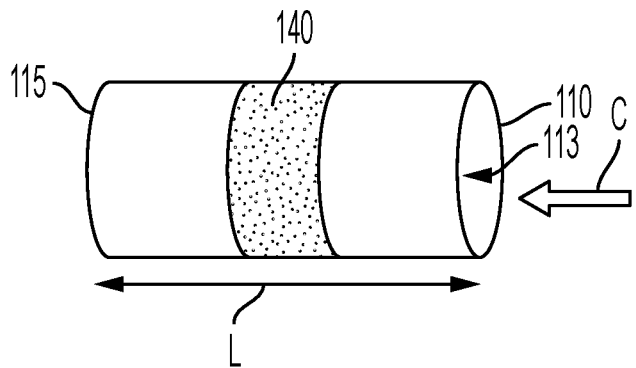
FIG. 3A shows a partial portion of an article from a side view indicating details of the holster.
Figure 3B:
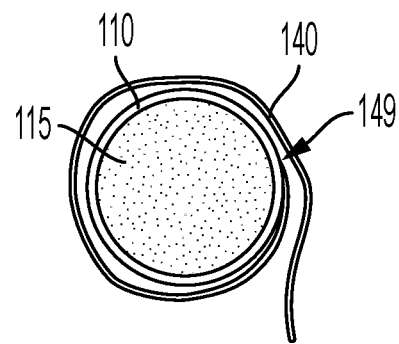
FIG. 3B shows a front view indicating details of the holster, having a fastener attached in loose configuration.

FIG. 3A shows a side perspective view indicating details of the holster 110. In some embodiments, the holster is comprised of the same soft material as the case. In some embodiments, the holster is made from a pliable fabric material. In some alternative embodiments, the holster may be comprised of a rigid material, or semi-rigid material, such as a tough yet pliable plastic. Holster 110 may be of a cylindrical shape or substantially cylindrical shape, having a longitudinal axis L. The holster 110 is formed within front side 104 (FIG. 1E) of the article, and extends into the interior region 121 (FIG. 1B) of the case 101. The holster has an opening 113, in which a sex simulation device, such as an artificial vagina masturbation device (such as the product sold under the registered trademark, Fleshlight®, owned by Steve Shubin, an individual), may be placed. The rear side 115 of the holster 110 is preferably closed off, to prevent excess movement of the sex simulation device during use. In some embodiments, however, the rear side is open. A fastener, represented as strap 140, is attached to, or disposed around, the holster 110. Strap 140 may be attached to holster 110 via a seam of stitching, hook and loop, buttons, or other mechanism at attachment point 149 (FIG. 3B). In embodiments, the strap 140 may include an elastic band, nylon strap, fabric strap, or other suitable material, which may be disposed around the longitudinal axis L of the holster 110.

FIG. 3B shows a front plan view indicating details of the holster 110 as viewed in the direction indicated by arrow C of FIG. 3A. The strap 140, attached at attachment point 149 to holster 110, is shown in relaxed, or loose, configuration. The back side of holster is shown at 115 (as viewed from the front/interior of the holster 110).

Figure 3C:
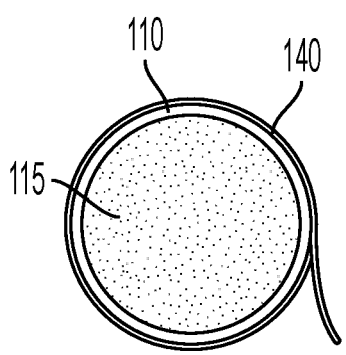
FIG. 3C shows another front view of the holster of FIG. 3B, having the fastener attached in tightened configuration.

FIG. 3C shows the holster 110 of FIG. 3C with the strap 140 tightened around the holster. In practice, a sex stimulation device would be positioned in the holster, and strap 140 would hold the sex stimulation device there within via force around the holster wall to the sex simulation device.

Figure 3D:
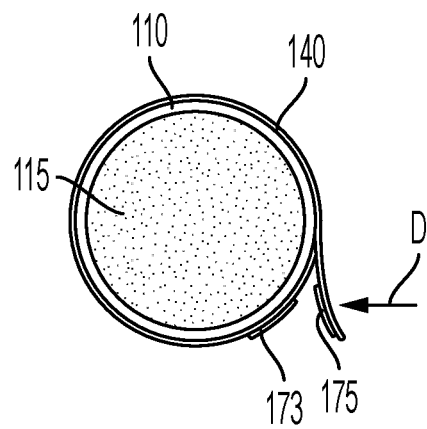
FIG. 3D shows another front view of a holster similar to that of FIG. 3C, having a strap attached in tightened configuration with a hook and loop closure for securing the strap.

FIG. 3D shows another embodiment of the holster 110 similar to FIG. 3C, except that a hook and loop fastener 173, 175 is on the strap 140 for securing the fastener in place. In some embodiments, the fastener/strap 140 may comprise a hook-and-loop fastener for securing a sex simulation device in place. Portion 173 has hooks and portion 175 has loops, and when portion 175 is pushed against portion 173 in direction D, the strap 140 is secured in place.

Figure 4:
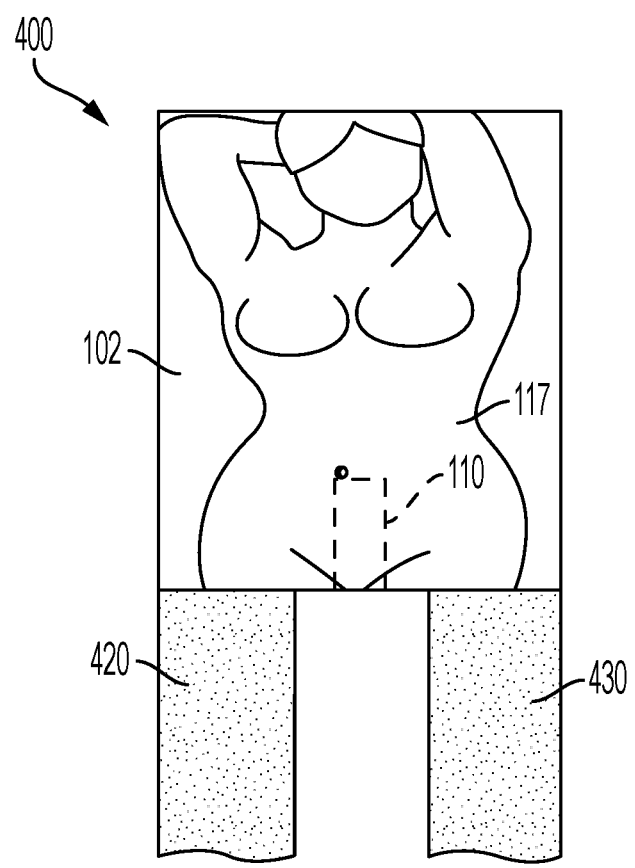
FIG. 4 shows a top-down view of an article in accordance with additional embodiments of the present invention.

FIG. 4 shows a top-down view of an article 400 in accordance with additional embodiments of the present invention. Article 400 is similar to article 200 shown in FIG. 2A and FIG. 2B, except that, instead of a single kneepad for both knees, two individual kneepads are used, indicated as kneepad 420 and kneepad 430. With this embodiment, the holster 110 is not blocked by the kneepads in case the user wants to switch between a top-down orientation of the article or a bottom-up orientation of the article. Thus, in embodiments that utilize a human image on the top side 102 and the bottom side 106, the article 400 can be oriented to expose either the top side 102 or the bottom side 106, and the dual kneepads 420 and 430 can still be used. Thus, embodiments can include two kneepads affixed to the first/front side of the case.

Figure 5A:
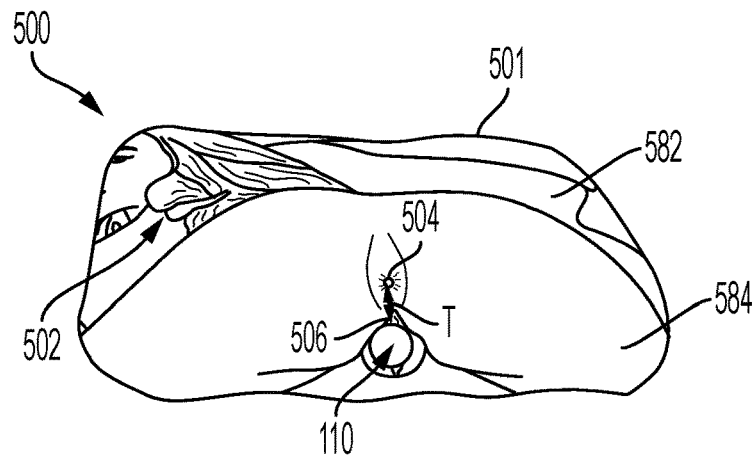
FIG. 5A shows a view of an article in accordance with embodiments of the present invention including an image including a rendering of an anatomical orifice.

FIG. 5A shows a view of an article 500, filled, in accordance with embodiments of the present invention having thereon a human image including a rendering of an anatomical orifice. Article 500 includes a case 501 having a human image 502 imparted thereon. In view, are a front side 584 and top side 582 of the article 500. The human image 502 includes a rendering of an anatomical orifice that is an anus 504 and a partial rendering of an anatomical orifice that is a vagina 506. The holster 110 is aligned with the rendering of the vagina 506. Furthermore, the location of the anus 504 to the holster 110 is in anatomical proportion, separated from the holster 110 by a distance T. In embodiments, distance T ranges from two centimeters to five centimeters. This means that the anus 504 is located, with respect to the holster 110, in such a way as to appear at the expected location where the anus of a human partner would appear for a person having sex with a partner in the sexual position indicated by the human image 502. In the embodiment shown in FIG. 5A, the user, during use, typically will not have visual contact with the holster 110, but will have visual contact with the anus 504, and thus, it is preferable that the orientation and sizing of the image 502 is such that, with respect to the location of the holster 110, the image of the anus 504 is in view during use, at the location indicated in FIG. 5A, which is proximate to the holster 110.

Figure 5B:
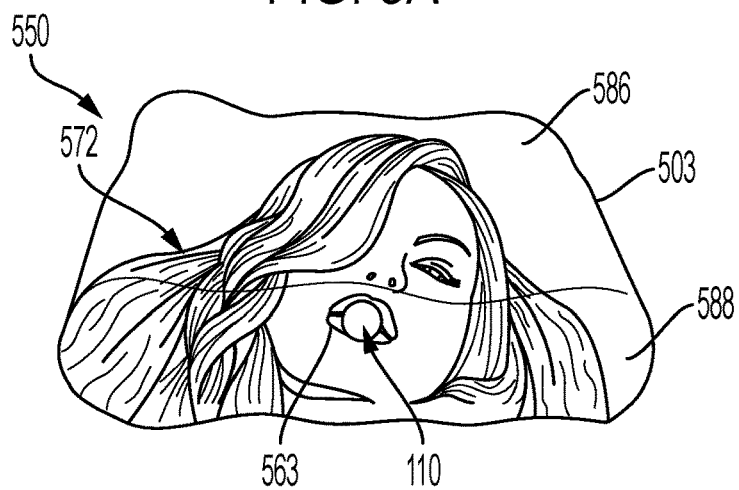
FIG. 5B shows a view of an article in accordance with additional embodiments of the present invention including an image including a rendering of an anatomical orifice.

FIG. 5B shows a view of an article 550, filled, in accordance with additional embodiments of the present invention having thereon a human image including a rendering of an anatomical orifice formed on the case 503. In view, are a front side 588 and top side 586 of the article 550. Article 550 is similar to article 500 of FIG. 5A, with the difference being the use of image 572 that has an anatomical orifice of a mouth 563 that is aligned with the holster 110. This embodiment provides an oral sex experience for the user. Other embodiments can provide a vaginal sex or anal sex experience, depending on which anatomical orifice is aligned with the e holster 110.

Accordingly, embodiments can include a case; a holster formed on a first side of the case, wherein the holster extends into an interior region of the case; a human image imparted on the case, wherein the human image includes a rendering of an anatomical orifice, wherein the human image is oriented such that the anatomical orifice is aligned with the holster. In embodiments, the anatomical orifice rendering is a vagina. In embodiments, the anatomical orifice rendering is a mouth. In embodiments, the anatomical orifice rendering is an anus.

Embodiments can further include a second human image imparted on the case wherein the second human image includes a rendering of a second anatomical orifice, wherein the second human image is oriented such that the second anatomical orifice is aligned with the holster. An example of an article comprising two images is shown in FIG. 1F and FIG. 1G, where FIG. 1F shows a first human image, and FIG. 1G shows a second human image on the opposite side of the first human image.

Figure 5C:
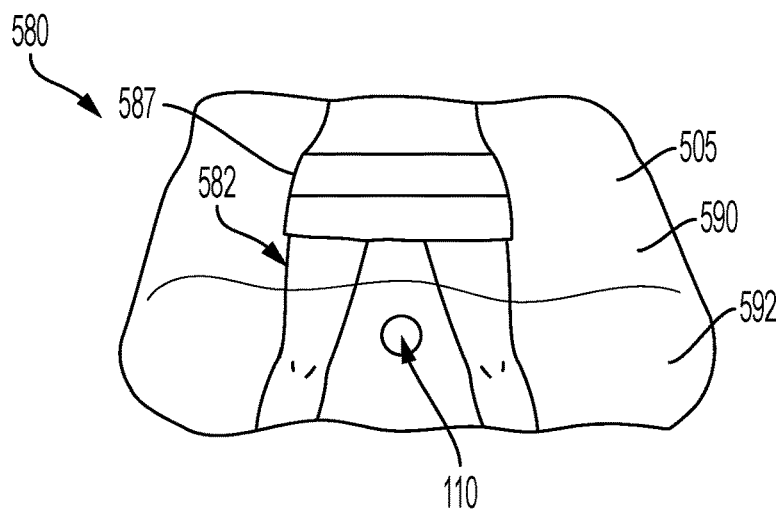
FIG. 5C shows a view of an article in accordance with additional embodiments of the present invention including an image without a rendering of an anatomical orifice.

FIG. 5C shows a view of an article 580, filled, in accordance with additional embodiments of the present invention including a human image 582 without a rendering of an anatomical orifice. In view, are a front side 592 and top side 590 of the article 580. In the example of FIG. 5C, the human image 582 is a person wearing a skirt 587. The skirt 587 is covering the area where anatomical orifices would appear. Although a specific anatomical orifice is not shown, the human image 582 provides sufficient detail for a user to estimate a location for an anatomical orifice. As long as the human image 582 is oriented such that the estimated location of the anatomical interface is located at or near the location of the holster, the user gets the visual stimulation of the human image while experiencing the tactile feeling of a sex simulator installed in the holster 110. Thus, in some embodiments, an anatomical orifice may not be rendered on the image. Instead, the human image may contain sufficient detail such that a user can deduce, in their mind, an estimated location of an anatomical orifice.

Accordingly, embodiments can further include a case; a holster formed on a first side of the case, wherein the holster extends into an interior region of the case; a human image imparted on the case, wherein the human image is oriented such that an estimated location of an anatomical orifice of the human image is aligned with the holster.

Figure 6:
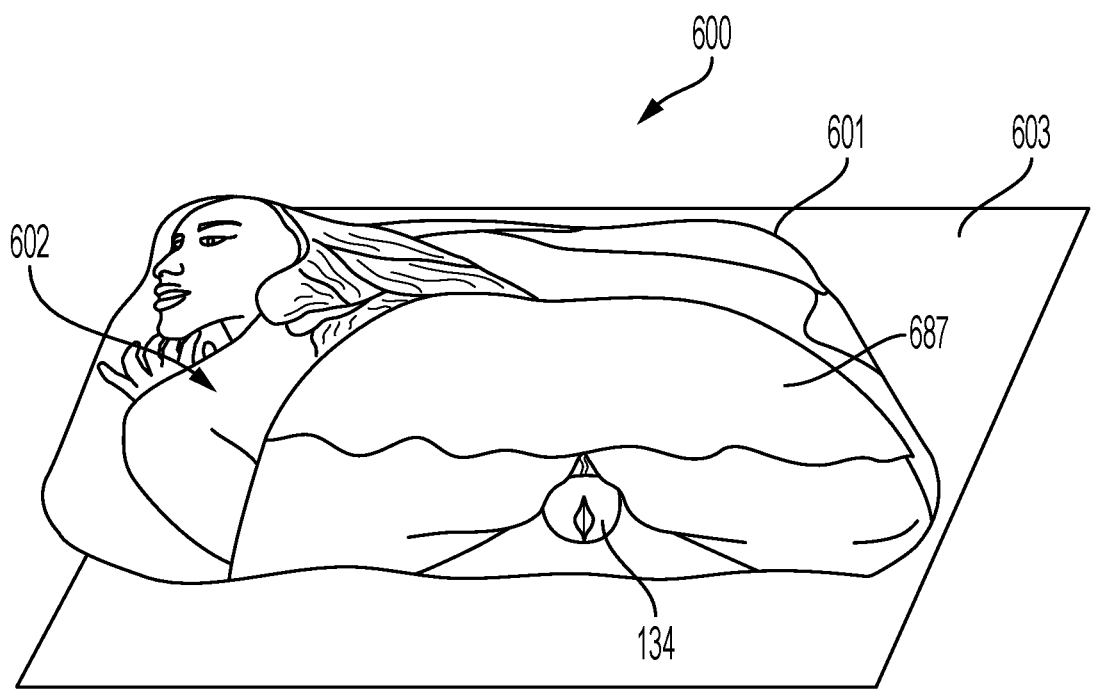
FIG. 6 shows another view of an article in accordance with embodiments of the present invention including an image including a rendering of an anatomical orifice.

FIG. 6 shows at an article 600, filled, in an example environment, in accordance with embodiments of the present invention including a human image including a rendering of an anatomical orifice. Article 600, shown positioned on a substantially flat surface 603, such as a floor or table, includes a human image 602 imparted thereon. The human in the image 602 is depicted, on case 601, wearing a skirt 687 that covers the anatomical orifice of the anus. A sex simulation device 134 is installed in the holster, the article is filled with fill material, and the holster (and therefore, sex simulation device) is aligned with the location of where the vagina of the human image 602 would be.

As can be seen in FIG. 6, once the article 600 is filled, and the sex simulation device 134 is inserted and secured in the holster, the article 601 is ready for use. A person user can insert their penis into the sex simulation device 134, while getting visual stimulation from the human image depicted on the case 601. Thus, embodiments can further include a sex simulation device, or masturbation device, installed within the holster.

Figure 7:
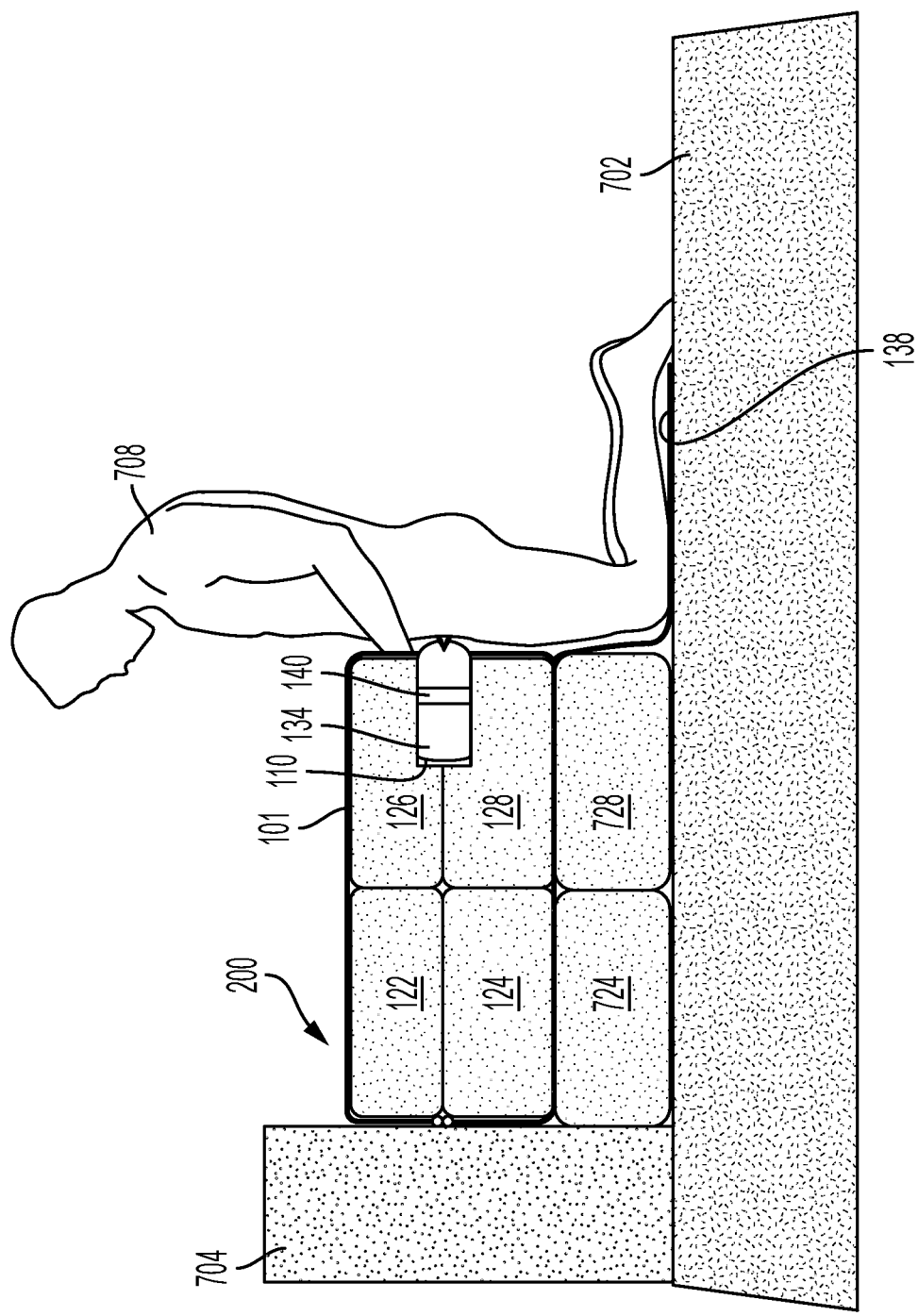
FIG. 7 shows an exemplary usage scenario of an article in accordance with embodiments of the present invention.

FIG. 7 shows an exemplary usage of a filled article 200 (of FIG. 2A) in an example environment in accordance with embodiments of the present invention. The article 100 is represented in cross-section to show the elements in the interior. In embodiments, a user may place the article 200 on a bed 702. In some embodiments, the article 200 may be placed above pillows 724 and 728, and placed adjacent to bed headboard 704. The user may place a sex simulation device 134 into the holster 110, and secure it with strap 140. The case 101 may be filled with multiple pillows, indicated as 122, 124, 126, and 128. The holster, including the sex stimulation device 134 therein, may be propped between the pillows 126 and 128 (or other fill material present) for stability. The user 708 may then insert their penis into the sex simulation device 134 to perform the process of masturbation and/or achieving sexual pleasure. In embodiments, the article may include a kneepad, such as 138. As can be seen in FIG. 7, the user 708 has their knees placed on kneepad 138, which is affixed to the case 101. The weight of the user 708 on the kneepad serves to further stabilize the article 200 during use. The user may hold onto the case 101 for greater stability, or in some embodiments, there may be handles, such as those shown in FIG. 2A and FIG. 2B as reference numbers 171a and 171b.

Figure 8A:
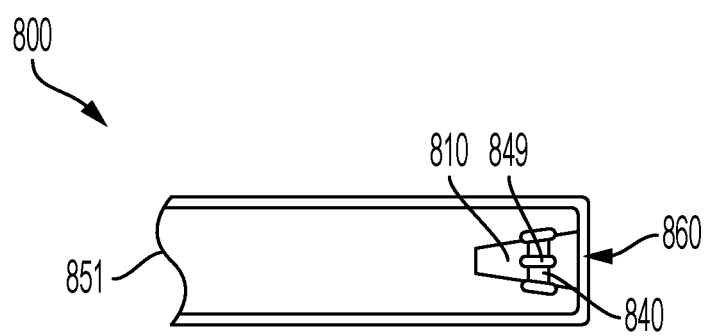
FIG. 8A shows an article with a holster in accordance with alternative embodiments of the present invention.

FIG. 8A shows a partial side view of an article 800 with a holster 810 in accordance with alternative embodiments of the present invention, with a wall removed so that the interior is visible. In embodiments, the holster 810 comprises a conical, or substantially conical, shape. It has opening 860 for insertion of a sex stimulation device. Line 851 is a break line. The holster 810 is shown expanded, wherein in practice a sex simulation device would be inserted therein, holding the holster in such position.

Figure 8B:
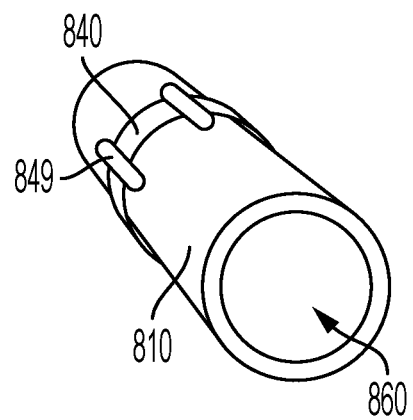
FIG. 8B shows a perspective detail view of holster of FIG. 8A, having a fastener disposed there around.

FIG. 8B shows a perspective detail view of holster 810, having a fastener disposed there around. In the example, the fastener is an elastic band 840. It is secured to holster via, for example, one or more fabric loops 849. It is shown expanded (as opposed to collapsed), wherein in practice a sex stimulation device would be inserted therein, holding the holster 810 open.

Figure 8C:
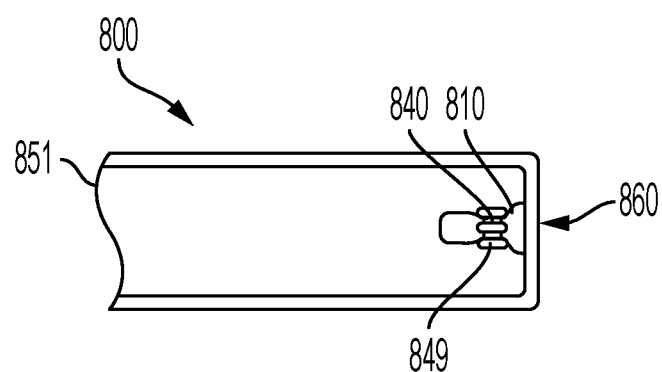
FIG. 8C shows a partial side view of an article of FIG. 8A with a side wall removed so holster is in view.

FIG. 8C shows a partial side view of an article 800 with a wall removed so holster 810 is in view. Holster 810 has elastic band 840 and loop 849 in view. The fabric of holster 810 is shown crushed as elastic band 840 has nothing to hold it open. It is expanded (like in FIGS. 8A and 8B) when a sex stimulation device is inserted there within. Elastic band 840 expands to hold the sex stimulation device in place. Line 851 is a break line.

Figure 9A:
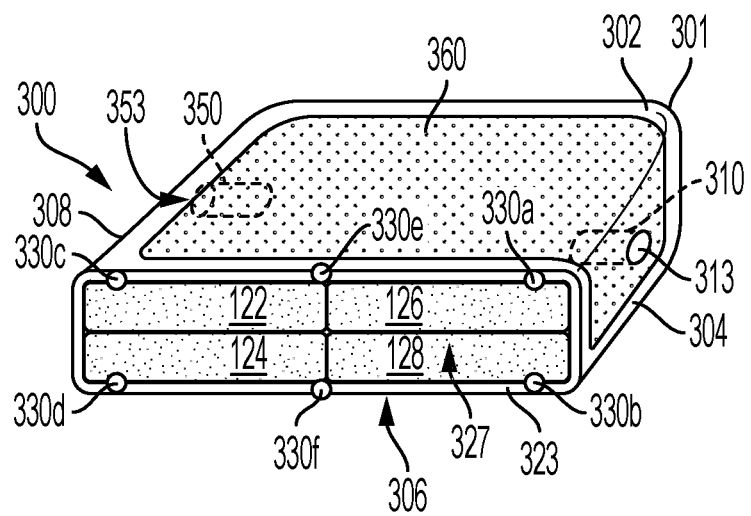
FIG. 9A shows an example embodiment having two holster in accordance with some embodiments of the invention.
Figure 9B:
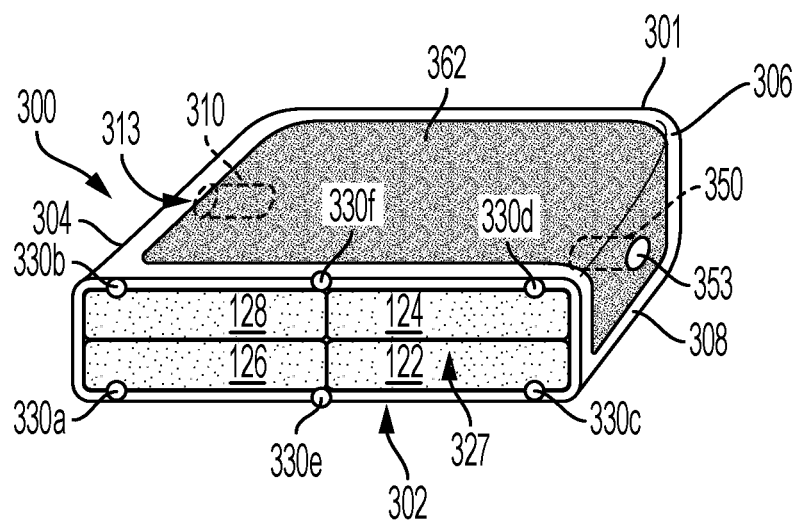
FIG. 9B shows the embodiment of FIG. 9A flipped over 180 degrees.

FIG. 9A shows a top-side front view of an example embodiment of article 600 where fill insertion opening 327 of case 601 is on a side wall 323, rather than opposite a holster (like in FIGS. 1A-1E). In the example, two holsters 310 and 350 are included disposed on sides 304 and 308 opposite one another. Each holster has an opening 313 and 353, respectively. Closures 330a-330e are shown, and are substantially similar to those of FIGS. 1A-1E. Pillows 122, 124, 126, and 128 are shown and are substantially similar to those shown in FIG. 1D. Box 360 represents a photograph or other illustration on top side 302. FIG. 9B shows the embodiment of FIG. 9A flipped 180 degrees so that bottom side 306 is facing up. As shown, another image 362 may be depicted on the bottom side 306 of the article 600. Embodiments, such as this example, allow the device to be used either by a single user with different images (360 and 362), each aligned to a sex simulation device, or by two users viewing a single image, each having their own sex simulation device. Accordingly, in some embodiments, more than one holster may be included on the article.

Figure 10A:
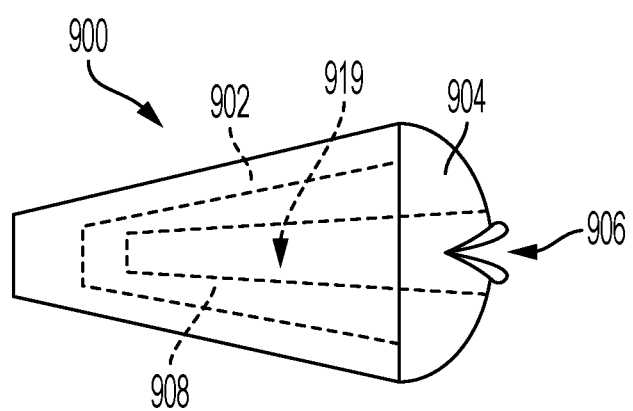
FIG. 10A shows a side view of an example of a conventional sex simulation device, which can be an artificial vagina, that can fit in the holster of embodiments of the invention.
Figure 10B:
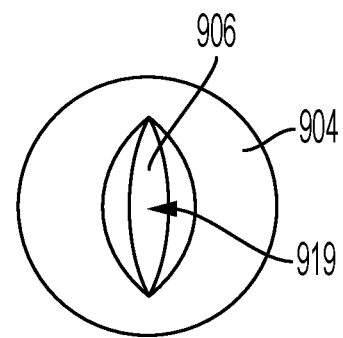
FIG. 10B shows a front view of an example of the conventional sex simulation device of FIG. 10A.

FIG. 10A shows a side view, and FIG. 10B shows a front view, of an example of a conventional sex simulation device, which can fit in the holster of embodiments of the invention. The device 900 has shell 902 extending around the sides, and a soft front 904. Opening 906 leads into the interior of device 900 where there is a canal 919 surrounded by a stimulation material 908, such as foam, silicone, or other suitable material for stimulation of a penis.

Figure 11A:
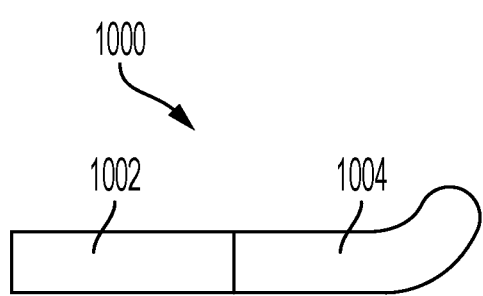
FIG. 11A shows a side view of an example of a sex simulation device, which may be a conventional dildo, vibrator, or other penetrative device, that can fit in the holster of embodiments of the invention.
Figure 11B:
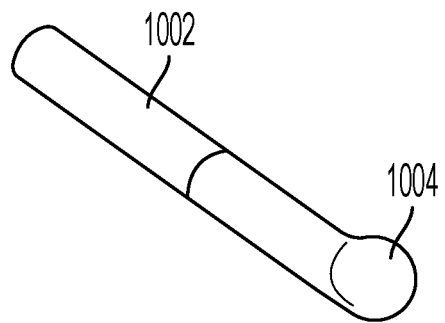
FIG. 11B shows a perspective view of an example of the sex simulation device of FIG. 11A.

FIG. 11A shows a side view, and FIG. 11B shows a perspective view, of an example of a sex simulation device, which may be a conventional dildo, vibrator, prostate massager, or other penetrative device, that can fit in the holster of embodiments of the invention. The device 1000 has handle 1002 extending around the sides, and a penetrative portion 1004. A user can insert the handle into the holster, and use the hard, or substantially-hard, penetrative portion for vaginal or anal penetration/insertion and stimulation.

As can now be appreciated, disclosed embodiments provide an improved user experience for a sex article. A photorealistic human image is formed on a textile such as a pillowcase. In some implementations, the photorealistic image is life-sized. A holster formed in the case secures a sex simulation device. The user fills the case with pillows or other suitable fill material. The user then is able to receive the tactile stimulation provided by the sex simulation device, along with visual stimulation provided by the human image. The human image is oriented such that an anatomical orifice, such as a vagina, anus, or mouth, is aligned with the holster. In this way, the visual user experience is a human image that appears to be in a sexual position as if the user was having sex with a real person, thus, heightening the sexual experience during masturbation. Embodiments are sanitary since they can be washed in a sink, or in some cases, in a washing machine, or via another suitable method. Furthermore, disclosed embodiments are portable. With the fill material removed, the case used with disclosed embodiments, and a corresponding sex simulation device can easily fit in an overnight bag. Thus, disclosed embodiments can be used while travelling. Thus, disclosed embodiments can serve to promote men's health by providing a safe and effective article to support frequent ejaculation and all the benefits that it brings.

While the invention has been particularly shown and described in conjunction with exemplary embodiments, it will be appreciated that variations and modifications will occur to those skilled in the art. The embodiments according to the present invention may be implemented in association with the formation and/or processing of structures illustrated and described herein as well as in association with other structures not illustrated. Moreover, in particular regard to the various functions performed by the above described components, the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of the invention.

What is claimed is:

1. A sex article, comprising:
a soft hollow case;
a holster attached on a first side of the soft hollow case, wherein the holster extends into an interior region of the case and wherein the holster is substantially cylindrical; and
an image imparted on the case, wherein the image includes a rendering of an anatomical orifice, wherein the image is oriented such that the anatomical orifice is aligned with the holster.

2. The sex article of claim 1, wherein the anatomical orifice is a vagina, a mouth, or an anus.

3. The sex article of claim 1, further comprising a fastener disposed around a longitudinal axis of the holster, wherein the fastener is within the interior region of the case.

4. The sex article of claim 3, wherein the fastener comprises a hook and loop fastening strap or an elastic band disposed around the longitudinal axis of the holster.

5. The sex article of claim 1, further comprising a second holster, and further comprising a second image imparted on a second side of the case wherein the second image includes a rendering of a second anatomical orifice, wherein the second image is oriented such that the second anatomical orifice is aligned with the second holster.

6. The sex article of claim 1, wherein the case is comprised of cotton, polyester, nylon, fabric, or textile.

7. The sex article of claim 1, wherein the image is formed by a process of dye-sublimation transfer printing.

8. The sex article of claim 1, further comprising a closure disposed on a second side of the case.

9. The sex article of claim 1, wherein the case is a pillowcase.

10. The sex article of claim 1, further comprising at least one kneepad affixed to a side of the case.

11. The sex article of claim 1, further comprising a sex simulation device installed within the holster.

12. The sex article of claim 1, wherein the holster is a sex simulation device holder.

13. The sex article of claim 1, wherein the soft hollow case further comprises primarily a non-gaseous filler.

14. The sex article of claim 1, further comprising a second image imparted on a side of the case adjacent the first side of the case, wherein the second image includes a rendering of a second anatomical orifice, wherein the second image is oriented such that the second anatomical orifice is aligned with the holster.

15. The sex article of claim 1, wherein the soft hollow case has the first side, a second side, and a third side, wherein the first side and the second side are opposite one another, wherein the third side is formed between the first side and the second side, and wherein an opening formed on the second side of the soft hollow case opposite the first side.

16. The sex article of claim 15, wherein the image imparted on the soft hollow case is imparted on the third side of the case.

17. The sex article of claim 16, wherein the first side and the second side are smaller in surface area than the third side.

18. The sex article of claim 14, wherein the rendering of the second anatomical orifice is the same as the rendering of the anatomical orifice.

19. The sex article of claim 14, wherein the rendering of the second anatomical orifice is different from the rendering of the anatomical orifice.

* * * * *